US012039850B2

(12) United States Patent
Simmons et al.

(10) Patent No.: US 12,039,850 B2
(45) Date of Patent: Jul. 16, 2024

(54) SYSTEM AND METHOD FOR FALL DETECTION USING MULTIPLE SENSORS, INCLUDING BAROMETRIC OR ATMOSPHERIC PRESSURE SENSORS

(71) Applicant: LogicMark, Inc., Louisville, KY (US)

(72) Inventors: Chia-Lin Simmons, Morgana, CA (US); Sean Powers, Melbourne, FL (US); Jonathan Larson, Novato, CA (US)

(73) Assignee: LOGICMARK, INC., Lousiville, KY (US)

( * ) Notice: Subject to any disclaimer, the term of this patent is extended or adjusted under 35 U.S.C. 154(b) by 0 days.

(21) Appl. No.: 17/972,389

(22) Filed: Oct. 24, 2022

(65) Prior Publication Data

US 2023/0125403 A1    Apr. 27, 2023

Related U.S. Application Data (60) Provisional application No. 63/271,194, filed on Oct. 24, 2021.

(51) Int. Cl.
*G08B 21/04* (2006.01)
*G06N 3/02* (2006.01)
*G06N 20/10* (2019.01)

(52) U.S. Cl.
CPC ............ *G08B 21/0446* (2013.01); *G06N 3/02* (2013.01); *G06N 20/10* (2019.01);
(Continued)

(58) Field of Classification Search
CPC ............ G08B 21/0446; G08B 21/0415; G08B 21/043; G08B 21/0492; G06N 20/10; G06N 3/02
See application file for complete search history.

(56) References Cited

U.S. PATENT DOCUMENTS 9,704,369 B2 * 7/2017 Richardson ........ G08B 21/0446
9,801,547 B2 * 10/2017 Yuen ..................... A61B 5/1118
(Continued)

FOREIGN PATENT DOCUMENTS

| JP | 2016177398 A | 10/2016 |
|---|---|---|
| WO | 2019067424 A1 | 4/2019 |
| WO | 2021032556 A1 | 2/2021 |

OTHER PUBLICATIONS

Pedregosa et al., "Scikit-learn: Machine learning in Python", The Journal of Machine Learning Research 12, 2011, 2825-2830.
(Continued)

*Primary Examiner* — Hoi C Lau
(74) *Attorney, Agent, or Firm* — Kilpatrick Townsend & Stockton LLP (57) ABSTRACT

A system, apparatus, and method to identify incentives in multi-party interactions where such incentives are represented by specification value pairs and through the use of game theory, machine leaning, pattern identification and recognition and/or digital twins in any arrangement, misalignment of such specification value pairs may be identified and responded to in manner that can avoid and/or mitigate the impact of such misalignments on the interactions of those parties, including in pursuit of the reduction of fraud or other undesirable behaviors within at least one system.

20 Claims, 3 Drawing Sheets

(52) U.S. Cl.
CPC ....... *G08B 21/0415* (2013.01); *G08B 21/043* (2013.01); *G08B 21/0492* (2013.01)

(56) References Cited

U.S. PATENT DOCUMENTS

| | | | | |
|---|---|---|---|---|
| 10,485,452 | B2* | 11/2019 | Orellano | G16H 50/30 |
| 10,588,519 | B2* | 3/2020 | Yuen | A61B 5/681 |
| 10,950,112 | B2* | 3/2021 | Ten Kate | G08B 21/0446 |
| 11,276,290 | B2* | 3/2022 | Tan | A61B 5/1123 |
| 11,282,361 | B2* | 3/2022 | Sharma | A61B 5/747 |
| 11,282,362 | B2* | 3/2022 | Tan | A61B 5/0022 |
| 11,282,363 | B2* | 3/2022 | Tan | A61B 5/747 |
| 11,380,181 | B2* | 7/2022 | Cheng | G01S 7/412 |
| 11,398,146 | B2* | 7/2022 | Yao | G08B 21/182 |
| 2003/0208335 | A1* | 11/2003 | Unuma | A61B 5/6831 |
| | | | | 702/141 |
| 2014/0278229 | A1* | 9/2014 | Hong | H04W 4/027 |
| | | | | 702/160 |
| 2014/0375461 | A1* | 12/2014 | Richardson | A61B 5/0002 |
| | | | | 340/573.7 |
| 2019/0103007 | A1* | 4/2019 | Tan | A61B 5/1117 |
| 2020/0250954 | A1* | 8/2020 | Tan | A61B 5/746 |
| 2020/0258365 | A1* | 8/2020 | Ten Kate | G08B 21/0446 |
| 2020/0342735 | A1* | 10/2020 | Tan | G01C 5/06 |
| 2020/0342736 | A1* | 10/2020 | Tan | A61B 5/1121 |
| 2020/0342737 | A1* | 10/2020 | Pham | A61B 5/1117 |
| 2021/0005071 | A1* | 1/2021 | Sharma | A61B 5/1121 |
| 2021/0052198 | A1* | 2/2021 | Parvaneh | A61B 5/1118 |
| 2022/0036714 | A1* | 2/2022 | Tan | A61B 5/746 |
| 2022/0180723 | A1* | 6/2022 | Cheng | G01S 13/62 |
| 2023/0125403 | A1* | 4/2023 | Simmons | G06N 3/08 |
| | | | | 340/573.1 |
| 2023/0326318 | A1* | 10/2023 | Saavedra | G08B 21/0453 |

OTHER PUBLICATIONS

PCT/US2022/047601, "International Search Report and Written Opinion", Jan. 24, 2023, 7 pages.

PCT/US2022/047601, "International Preliminary Report on Patentability", May 10, 2024, 5 pages.

* cited by examiner

SYSTEM AND METHOD FOR FALL DETECTION USING MULTIPLE SENSORS, INCLUDING BAROMETRIC OR ATMOSPHERIC PRESSURE SENSORS

CROSS REFERENCE TO RELATED APPLICATIONS

This application claims priority to U.S. Provisional Application No. 63/271,194, filed on Oct. 24, 2021, and the contents of which is incorporated herein by reference.

BACKGROUND

Field of the Disclosure

Aspects of the disclosure relate in general to a device, system and method to reduce false positive in fall detection using multiple sensors.

Description of the Related Art

According to the World Health Organization, a fall is defined as an event that results in a person inadvertently coming to rest on the ground, a floor, or at a level below a starting height or orientation (e.g. vertical/standing to horizontal/on the ground). Several factors can indicate the occurrence of a fall such as changes in height, changes in direction, changes in motion speed, and detection of an impact.

Of the 35 million Americans over 65, about 1 in 3 will fall in a given year, and 50% of those people who fall require assistance from someone else to get up. Seniors are hospitalized for fall-related injuries 5 times more often than they are for injuries from all other causes. Falls are the leading cause of accidental death for seniors.

Research shows that prompt help increases the likelihood of surviving such an emergency. If quick help can be summoned, a senior citizen is more likely to continue living independently. To the contrary, the longer a person spends in a helpless situation (e.g., having fallen but unable to return to an upright position) the greater the likelihood he/she will be discharged to supportive care. For elderly people who live alone, becoming incapacitated and unable to get help is a common worry, which usually marks the end of their independent living. After a fall or other emergency, 90% of people who get help within one hour will continue independent living, but if the help does not arrive for 12 hours only 10% of those people will continue to live independently at home.

Current fall detectors can be divided into two categories: shock or impact detection and orientation sensing. In the first category the device must experience a measurable shock (from an impact, for example) from which a fall is identified. Devices in the second category commonly uses a tilt switch (mercury switch) and require the user to wear the object oriented such that when he/she is in a horizontal orientation the tilt switch triggers. Both the first and second type can also include gyro and accelerometers.

SUMMARY

A wearable device comprises a machine-learning fall detection processor, a non-transitory computer-readable medium, a plurality of motion sensors, at least one height sensor, and a force sensor. The non-transitory computer-readable medium has a database configured to store an expected activity level of the wearer. The plurality of motion sensors, each motion sensor having an individual fall motion threshold, the motion sensors sends a fall motion signal to the fall detection processor when the individual fall motion threshold is exceeded. The at least one height sensor has a fall height threshold. The at least one height sensor sends a fall height signal to the fall detection processor when the fall height threshold is exceeded. The force sensor has a force threshold. The force sensor sends a force signal to the fall detection processor when the force threshold is exceeded. The fall detection processor issues an alert when a minimum number of sensors from among a total number of sensors of the plurality of motion sensors, the at least one height sensor, and the force sensor indicate a fall has taken place. The minimum number of sensors is set automatically by fall detection processor based in part on the expected activity level of the wearer. The fall detection processor updates the expected activity level of the wearer stored in the database with an actual activity level of the wearer.

A wearable device executes a fall detection method. A non-transitory computer-readable medium stores an expected activity level of a wearer in a database. A fall detection processor receives a fall motion signal from a plurality of motion sensors, each with a fall motion threshold, when the individual fall motion threshold is exceeded. The fall detection processor receives a fall height signal from at least one height sensor having a fall height threshold when the fall height threshold is exceeded. The fall detection processor receives a force signal from a force sensor having a force threshold when the force threshold is exceeded. The fall detection processor issues an alert with the fall detection processor when a minimum number of sensors from among a total number of sensors of the plurality of motion sensors, the at least one height sensor, and the force sensor indicate a fall has taken place. The minimum number of sensors is set automatically by fall detection processor based in part on the expected activity level of the wearer. The fall detection processor updates the expected activity level of the wearer stored in the database with an actual activity level of the wearer.

A non-transitory computer readable storage medium is encoded with data and instructions. When executed by a fall detection processor causes a wearable device to execute a fall detection method. A non-transitory computer-readable medium stores an expected activity level of a wearer in a database. A fall detection processor receives a fall motion signal from a plurality of motion sensors, each with a fall motion threshold, when the individual fall motion threshold is exceeded. The fall detection processor receives a fall height signal from at least one height sensor having a fall height threshold when the fall height threshold is exceeded. The fall detection processor receives a force signal from a force sensor having a force threshold when the force threshold is exceeded. The fall detection processor issues an alert with the fall detection processor when a minimum number of sensors from among a total number of sensors of the plurality of motion sensors, the at least one height sensor, and the force sensor indicate a fall has taken place. The minimum number of sensors is set automatically by fall detection processor based in part on the expected activity level of the wearer. The fall detection processor updates the expected activity level of the wearer stored in the database with an actual activity level of the wearer.

BRIEF DESCRIPTION OF THE DRAWINGS

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evident to the contrary from the description, where elements in different figures use identical reference numbers, the elements are generally either identical or at least similar in function or purpose.

DETAILED DESCRIPTION

Aspects of the present disclosure include a personal emergency response system (PERS) that detects when a person has fallen, as determined by measurements from multiple sensors. In such cases, the personal emergency response system is integrated in a pendant, watch, glasses, or other wearable device. The PERS may include a pressure sensor for tracking the height of the sensor above a reference. One or more of the sensors may be capable of operating in a low-power environment to conserve battery power.

Another aspect of the disclosure is the recognition that a PERS wearer can receive a shock or impact when she merely bumps into a counter or table when walking through her home. Also, when one has a serious event (e.g., a sudden cardiac arrest), the person may not fall violently to the ground. Instead, the person may, for example collapse slowly to the ground, grasping at nearby objects to cushion the fall. Such a slow fall may not trigger the shock or impact sensor.

Also, consider that the tilt sensor must be disabled each time the wearer wants to lie down (e.g., to take a nap or go to bed for the evening).

Besides accurately detecting a fall and then signaling for emergency assistance, false positive fall detections (i.e., the PERS detects and indicates a fall event, but the wearer did not fall) are major problems with current fall detection PERS. If the PERS frequently signals a fall event—when a fall did not occur—the user's confidence erodes and may deter the user from using or carrying the PERS. It is estimated/rumored that 30-50% of fall detection features are disabled within PERS after the device has been deployed because of these false positive alerts.

It is well-known that determining if a monitored person has fallen is a difficult problem. According to one embodiment of this invention, multiple sensors are employed to improve the probability of accurate fall detection and limit the number of false positives. It is critical to determine whether the monitored person is about to fall or has fallen; the more sensor inputs that are available, the more definitive the answer. Certain sensors can provide a more accurate indication of a fall while other measured values are less reliable in fall detection systems. Therefore, the most accurate PERS use several sensors, considering (including weighting) each measured value, for example as a data value pair, array, set of other data format, as appropriate to improve their accuracy in fall detection. Several such systems are described below.

One promising fall detection technique uses AI/ML (artificial intelligence/machine learning) decision process with data supplied from multiple sensors, each supplying data to be used in the AI/ML decision-making process. This data can form a rich corpus for the ML/AI techniques and subsequent decision-making processes.

The use of AI/ML techniques includes, for example the identification of data that represents a change of state of the sensor providing such data and the probability that such data, in part or in while could indicate a fall. The ML/AI may detect feature sets that are represent such changes of state and/or may be precursors to those state changes.

Additionally, as described further below, the PERS uses comparative data and data patterns from a community of PERS users as another input to the fall detection process for a monitored person. The monitored person's historical movements, activities and data patterns, as well as data patterns from the community at large, are also used as determinates of a fall event. The application of ML/AI techniques to a corpus of community data supports the identification of repeating activities for a monitored person and the contextualization of those activities in comparison to a community.

For example, a PERS AI/ML based algorithm looks at data from others of similar age, gender, health, as well as time, day, etc. to determine whether similar patterns lead to similar potential fall situations or to a fall event. This creates a corpus of sufficient data for ML/AI, —where such techniques as similarity evaluation, matching and comparison, predictive, Bayesian, fuzzy logic, recursive, deep learning and other techniques may be applied, to provide an adaptive decision processing system. The aggregate group can be expanded and/or extended to include people of, different gender, health, age, weight, etc., if there is a similarity in the measured data patterns. For example, the system can review cohorts that are not similar in age, health, gender, etc., but present similar data that then led to a fall event. Such identification of similarity can employ machine learning feature detection techniques.

Sensors commonly included within a PERS can easily detect a change of direction (gyroscope), a change of speed (accelerometer), an impact (accelerometer detecting a sudden stop (i.e., speed suddenly decreased to zero)) and a tilt or inclination (tilt switch). But determining the devices' starting orientation and/or height before the fall event can be problematic, especially since the detection device may be worn or carried in any one of several locations, each of which is likely a different distance from a ground level or floor (a reference level). For example, the PERS may be worn on a wrist, on a lanyard, or clipped to clothing or in other manners be worn by the monitored person. Additionally, the PERS wearer's height must be taken into consideration, in so far as this may contribute to establishing at least one height reference, where such a height reference may be used as part of a fall detection evaluation.

But each of these locations is a different distance from the reference floor height. Variations in these parameters, such as those found in many circumstances, may be evaluated and used as, in part or in whole, data for adaptive decision systems, such as those measuring rate of change variations in an environment to establish differential values, which are essential to accurately detect a fall with a low false alarm rate, and can make such an accurate detection difficult. A reference height cannot be determined from common PERS components, such as using an accelerometer, gyroscope, or tilt switch, however without this reference height information (i.e., distance to the ground or floor on which the wearer is standing) it can be difficult to accurately determine if a person has experienced a fall.

One embodiment of the present invention uses an atmospheric pressure sensor that periodically determines and stores the pressure data in a FIFO (first in first out) memory buffer, which enables the system to evaluate data prior to, for example, and occurrence of a possible fall, for example one indicated by at least one other sensor. The data is also sent to a cloud-based backup memory. The time the pressure was measured is also recorded for comparison with the timing of other events (e.g., acceleration, impact events, such as those data provided by other sensors). Height information can be easily determined from the atmospheric pressure. The height information derived from the pressure measurement can be used to determine the reference level or reference floor height. If after the reference level is determined, a subsequent height value is determined to be within a few inches of the reference height, then this is one indicator that the monitored person may have fallen.

In one embodiment the pressure sensor comprises a low power pressure sensor to conserve battery power.

Cloud back-up of measured values and data can occur when the PERS is at full power and during "sleep" (low power) periods. Timing of data back-up to the cloud is also variable and, like data measurements, may depend on the activity level of the monitored person or other relevant factors.

The rate at which the pressure data (and other sensor data) is determined is variable and may depend on the activity level of the monitored person, on concurrent measured values, and/or on prior measured values. For example, once per hour may be sufficient for measuring pressure and other fall-indicator values during periods of low or light activity, while a more active monitored person may require measuring the pressure and other fall-indicator values more frequently.

The sensed pressure may be a function of temperature and thus in certain embodiments it may be necessary to correct the pressure measurement based on ambient temperature.

When the wearer (monitored person) is within a predefined geo-fence area (for example, lying on a bed) the rate of data collection may also be reduced.

Also, the measurement duration (i.e., interval during which the sensor remains on to collect data) is variable and may depend on various factors that contribute to the fall detection process, including the configuration of sensors and the system receiving the data and providing the monitoring capability. The rate at which data is collected is also variable as dependent on various configuration and other factors.

Also, the monitoring period may be divided into time slices, with certain predetermined sensors activated during each time slice. Or different sensors may be activated in different time slices. Such an approach can ensure that a set of sensors may be operating in a manner so as to provide sufficient data so as to be able to determine the conditions for evaluation of a fall condition, including any false positives.

The order in which the sensors are activated is also variable and can be wearer dependent. It may be advantageous, for example, to first check the pressure sensor. If it indicates no change from the prior reading, then it may not be necessary to measure acceleration or other fall-detection parameters.

Use of low-power sensors, according to one embodiment, conserves battery power and allows the main processor (that analyzes the pressure data and other sensor data) to remain in a "sleep" or low power state while the data is collected. When one of the low-power sensors (detecting acceleration, impact, rotation, motion, etc.) within the PERS detects conditions that are possibly indicative of a fall, the processor is awakened for further analysis of the measured data.

In another embodiment, battery capacity in the PERS is sufficient to permit all sensors to operate or to be in an active state at all times. Additionally, if battery capacity is sufficient, the processor can also remain awake at all times, except, perhaps, when the monitored person is sleeping or otherwise engaged in low-motion activities. Sensor state may be varied in light of battery capacity, without reducing sensor coverage of a potential fall condition. That time may be ideal for recharging the PERS batteries.

Each of the sensor measurements (e.g., acceleration, impact, rotation, angular velocity) is analyzed by a processor relative to predetermined threshold values (obtained from a lookup table of fixed values or created using AI or machine learning techniques or based on prior sensed/measured values) and the time at which the measurement was taken. For example, this may be embodied as a graph database, schema or read or schema on read database. These threshold values are generally indicative of a fall and thus if one or more is exceeded, the processor accesses the atmospheric sensor measurements from the FIFO memory buffer (and/or from a cloud based memory from which the PERS can download needed data and operating instructions) and compares the atmospheric data gathered before, during, and immediately after the detected event. Here too, thresholds may be employed (static or dynamic values). A sudden change in atmospheric pressure (height) is an indication of a fall, especially when supported by other sensor data analyzed by the processor.

The atmospheric pressure data and the acceleration, impact, rotation, speed, etc. data are analyzed relative to their respective thresholds and the relative timing of each measurement to determine whether to classify the event as a fall. Such a combination of sensor data provides for effective detection of falls and of false positives, where one or more sensors data have changed from their threshold values, however such changes are not confirmed or are contradicted by other sensor data. For example, comparing atmospheric pressure data before, during, and after a possible fall event can more accurately determine whether a fall has occurred, especially when evaluated in light of data related to direction of motion (i.e., only along a horizontal axis or both horizontal and vertical motion, which can be determined from pressure/height data), motion speed (an immediate change or slowly crawling into bed) and impact.

The threshold values and timing of measurements may also be based on profiles created for users who are classified within different classes. For example, different profiles, and therefore different thresholds and measurement timing, may be created for adults, senior citizens, teenagers, babies, etc. And the parameters that are sensed or measured may also be dependent on a class into which the wearer falls.

Such personal information can be easily collected prior to first use of the PERS and continuously gathered thereafter. Various data thresholds, data patterns, timing of data collection and sensor measurements, etc. can then be automatically implemented within the PERS, resulting in more accurate fall detection.

In addition to the personal information, a profile is created for the monitored person. The profile identifies characteristics of the monitored person that are relevant to fall detection, such as daily activities, normal gait, normal heart rate, etc. Such a profile can be used, in part or in whole to configure the at least one threshold, patterns, timing data and/or sensor and system parameters Such alignment of the profile comprising the personal information, supports the identification of false positives which otherwise could be overlooked, triggering unwanted events.

Also, different fall profiles suggest that different information may be required to definitely determine that a fall occurred. For example, the following fall profiles suggest the need for different measurements and analysis techniques: tumble or fall forward, take a few blocks then fall, walking then fall, fall to knees, fall on the wearer's buttocks, and fall on the wearer's side.

In the context of a machine learning/artificial intelligence embodiment (see further details herein) collected data that is linked to a fall is stored in a database (on board at least one devise and/or in the cloud). Later, a fall is indicated when current data is highly correlated with that prior data. This use of fall data comprising the data of an actual fall, may be used, using ML/AI in the detection of false positives and may incorporate data sources such as those of a profile including patterns thereof.

The PERS also includes a "learning" feature wherein the software "remembers" that if for example, the wearer engages in vigorous exercise every day between 10 and 11 AM. Such information may be incorporated into a wearer's profile. The PERS processor thus discounts (or assigns a low weight (see the discussion of the neural network embodiment herein) to certain measurements taken during that hour. In addition to the PERS learning the times of vigorous activity of the monitored person from repeated occurrences at about the same time each day, the monitored person can manually set the PERS based on expected vigorous activity during future days/times. Finally, immediately prior to engaging in vigorous activity, the monitored person can manually adjust the PERS (sensor threshold values, for example) so that certain sensor measurements are ignored or the effect of a measured value is discounted relative to other sensed values from other sensors. This control feature may change (e.g., increase) thresholds for certain measured parameters that would be directly affected by vigorous activity. This may be presented to the wearer in the form of an application, including a wellness dashboard which can modify the user profile settings. Such modification may be stored on the device and/or in the cloud, such that they can be recalled and/or used by the machine learning techniques to further extend and/or enhance that profile.

Thus, the system learns in the sense that past behavior (especially past repetitive behavior) influences current thresholds and analyses. If for several days at 10 AM the wearer drops down low during a yoga routine, and the fall notification issued after each such "fall" is canceled by the wearer (because she had not fallen) the PERS retains that information. Later "falls" at about 10 AM are discounted and other measured data relied upon to indicate a fall. This can significantly decrease the number of false positives that are detected, enhancing the overall operation of the system to the benefit of the wearer and any systems, such as emergency services, medical or care teams and the like.

In addition to using the time-of-day as a parameter in determining that a fall occurred (or did not occur) the wearer's location can also be considered. The PERS includes a location determining device (for example, a GPS receiver or using a signal triangulation technique). If the determined location is a gymnasium or yoga studio, then measured tilt values or other measured values indicative of vigorous activity are discounted. When the wearer leaves the gym or yoga studio (as determined by the location-determining device) the measured tilt values are given more weight in analyzing any subsequent fall event occurred.

The fall determination algorithm within the PERS can be modified (either manually by the monitored person or automatically based on prior fall or no fall determinations) to make it more sensitive to certain sensors under certain conditions and less sensitive to certain sensors under other conditions, such that more accurate fall determinations are made and fewer false positives alerts are issued. This adaptive approach to reduction of false positives provides significant benefits in the performance of the systems and the inherent reliability and subsequent trust placed in the events triggered by those systems While the conditions that govern that sensitivity are many, several have been described herein and include, for example: time of day, activity level of the monitored person, location of the monitored person, expected future activity level or location based on prior activity level or location at the same time of day.

The conditions and measured data that had served as the basis for issuing a fall alert, that was subsequently nullified, are stored for later comparison with measured parameters. A high correlation between the past data that generated the false alarm and current data is a good indicator that a fall has not occurred, but also suggests that additional sensor data is warranted for more accurate fall detection, to reduce the number of false positives In another embodiment, when the processor wakes up, it analyzes measurements obtained from all sensors, including the pressure sensor. By analyzing all sensed data, this embodiment is distinguished from the embodiment presented above wherein the pressure data is analyzed only if certain other measurements result in a tentative conclusion that a fall has occurred.

Upon detecting a fall, the PERS issues an alert or notification reporting the fall, including a request for emergency assistance. The notification can be issued to parties identified by the wearer and/or emergency personnel.

In addition to the advising that the wearer has fallen, the alert can include additional information related to the fall, such as location, time of the fall, direction in which the wearer fell, intensity of the fall impact, current heart rate, current respiration rate, and any other data generated by the sensors in any arrangement.

In addition to low-power sensors, as described herein, in one embodiment, the PERS may also comprise a low power transmitter. Typically, such transmitters have a limited signal coverage range and therefore can communicate only with nearby devices. In such an embodiment the low-power transmitter issues an alert (the monitored person has fallen, for example) to a nearby device that operates at a higher power level and therefore has a larger signal coverage area. The latter, high power device then issues the fall notification to parties designated by the monitored person, for example, family members and emergency responders. E.g.—Bluetooth and WiFi If sufficient power is available to the PERS, a low power transmitter is replaced with a high-power transmitter such that the fall notification can be issued directly to emergency personnel, family members, etc. via a mobile telephone service or a proximate WiFi router that sends the notification signal to identified receiving parties via the Internet (e.g., email and text notifications).

As described, by recording/storing, buffering, and analyzing sudden changes in atmospheric pressures, a PERS can confirm a fall by comparing the height (atmospheric change) before and after the detected fall event. This atmospheric pressure change, along with initial detection of a fall using other sensors, can confirm if a person has experienced a fall. Being able to compare atmospheric pressure before, during and after a fall event can help accurately confirm if the direction, speed and impact was experienced in only in the horizontal axis or if it included motion and distance in the vertical axis.

Placement of Sensors

The sensors and/or processing components of the various described embodiments can be enclosed in a wearable, enclosed in a pendant, or affixed to clothing. Generally, a wearable comprises an electronic device that can be worn as an accessory, embedded in or attached to clothing, implanted in the wearer's body, and/or tattooed on the skin in any arrangement. For example, such a device may incorporate sensors worn on the skin that connect to further sensors and/or devices carried as a pendant Such electronic devices can also be enclosed within, for example, an article of clothing, shoes, a hat, a head band, glasses, a hearing aid (especially attractive because the hearing aid includes multiple electronic components, some of which can be used to function as a PERS), a choker, a bracelet, a necklace, a ring, a wristwatch (that is, any jewelry item), a belt, a tie clasp, earbuds, and a GPS tracking device. Although not strictly considered a wearable, any device that is commonly carried by the user (such as a mobile phone or keys) can also be adapted to perform the functions of a PERS.

Figure 1:
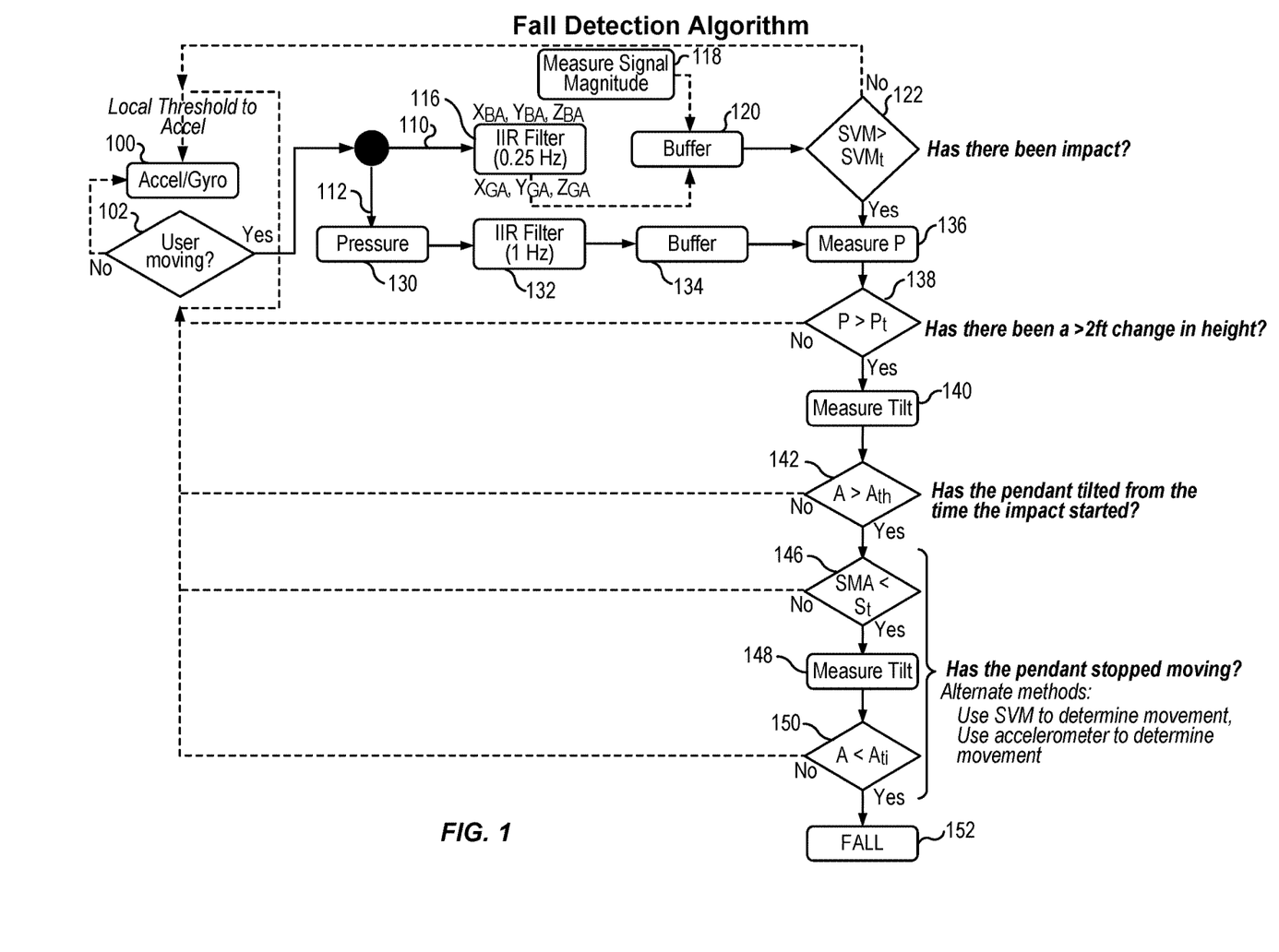
FIG. 1 is a block diagram of a personal emergency response system (PERS) that detects when a person has fallen, as determined by measurements from multiple sensors.

Description of FIG. 1 Embodiment

FIG. 1 presents another fall detection algorithm. A PERS is worn by a monitored person and accelerometer/gyroscope 100 senses/measures acceleration and direction of the acceleration. At a decision block 102 the measured values are analyzed to determine whether the wearer has moved. If not, processing returns to the measurement block 100. Thus, the blocks 100 and 102 determines whether there has been any movement of the monitored person and if not, there is no need to further process measured values or in fact, to measure values that can be indicative of a fall, however such values may be recorded as part of the profile or pattern for that person But if it has been detected that the monitored person has moved, processing moves from the decision block 102 to dual paths 110 and 112. The path 110 measures or determines a signal vector magnitude that is essentially an estimate of the degree of movement intensity in each one of three axes or directions, X, Y, and Z. Here the signal vector magnitude is the square root of the sum of the squares of each of these three component values. Thus, movement or motion along each axis contributes equally to determine the signal vector magnitude and then based on that value whether or not there has been an impact.

As can be seen, the determined signal vector magnitudes in each of these three directions is processed through an infinite impulse response filter 116 and the signal vector magnitude is determined at a block 118. The results from the block 118 are buffered in a buffer 120. At a decision block 122 the calculated signal vector magnitude is compared to a signal vector magnitude threshold. If the result from that decision block is negative, processing returns to the blocks 100 and 102 to again determine movement or motion by the monitored person.

If the result from that decision block is positive, processing continues to a block 136, as described below.

Along the path 112 pressure is measured at a block 130, filtered through an infinite impulse response filter 132, buffered in a buffer memory 134. The final pressure value determined at the block 136 is compared to a threshold pressure value at a decision block 138. If the response from the decision block 138 is affirmative, this indicates that there has been at least 2 feet change in height at the location of the PERS.

If the decision at the decision block 138 a is negative, processing returns to the initial blocks 100 and 102.

Note that the result of the impact analysis (the decision block 122) also leads to the pressure measurement block 136.

If the decision from the decision block 138 is affirmative, processing moves to a block 140 where the tilt value is determined. At a decision block 142 the determined tilt value is compared with a tilt threshold. A negative response from the decision block 142 indicates that the pendant or PERS has not tilted from the time the impact was determined. An affirmative response from the decision block 142 indicates that there has been some tilt of the PERS, which may indicate that the wearer has fallen, thereby resulting in a tilting orientation of the PERS wearer. Processing then continues to a decision block 146.

At the decision block 146, a signal magnitude area (SMA) parameter is compared with a threshold. The SMA is another parameter for determining the intensity of the activity of the wearer and thus can be used to distinguish between rest and movement of the wearer.

It is noted that both the SVM and SMA values can be used for determining movement. The SVM is a real-time value based on the current (or buffered) acceleration value so it can determine quick changes and movement (or impact). The SMA value is an area under a curve to help determine movement intensity. This is done over short period of time (such as one second) to determine how much movement occurred during that period. It is therefore used to help determine if the user is moving after a fall event.

If the result from the decision block 146 is affirmative, processing moves to a block 148 where the tilt is again is measured. This is followed by the decision block 150 where the measured tilt parameter is compared again to the tilt threshold. The objective now to determine if the wearer has stopped moving and thus the tilt value must be less than a tilt threshold to generate an affirmative response at the decision block 150. A fall is indicated at a block 152 following an affirmative response from the decision block 150.

Note that a negative response from the decision block 138, 142, 146, and 150 returns processing to the blocks 100 and 102.

The data generated through these blocks can be stored in at least one repository to form a corpus for at least one machine learning technique to be operated upon, for example to detect feature sets that indicate a fall or a no fall. These feature sets may then be compared to the data generated in real time to predict and/or identify the probability of a fall, increasing the accuracy of fall detection and false positives thereof.

Accelerometer and Gyroscope Embodiment

A pendant or PERS can include an accelerometer (i.e., a triaxial accelerometer) that detects either velocity changes or changes in direction. A second sensor is a gyroscope that detects changes in the orientation of the wearer, more specifically changes in the direction of the pendant that encloses the gyroscope. If, for example, a gyroscope is worn on the wearer's belt or lanyard, and the belt or lanyard changes direction, this is another indication that a fall may have occurred. Using the accelerometer sensor measurement and the gyroscope sensor measurement provides more accurate fall detection.

In one embodiment, if either the accelerometer or gyroscope measurement exceeds a threshold, then another sensor is activated. Or if both the accelerometer and gyroscope measurements exceed their respective thresholds, then another sensor is activated. Using two or more sensed values to determine whether a fall occurred is an improved approach over use of a single sensor.

If a change in orientation or direction, as detected by the gyroscope, occurs immediately following a change in an acceleration, as determined by the accelerometer, then this is a further and more definitive indication that the wearer has fallen.

In the event that both the accelerometer and gyroscope generate a signal that indicates a potential fall, yet a third sensor can collect additional information to make the fall determination more reliable. In such a case, the third sensor may be a height sensor that uses atmospheric pressure values to determine its height above sea level or above a reference height. When the wearer is standing upright, the pressure sensor/height detector measures a first pressure value. If the wearer falls the height pressure sensor measures a second pressure value, which is lower than the first measured pressure value. While a simple change in pressure value may indicate that the wearer has fallen, (or has just laid down) clearly use of the accelerometer value and the gyroscope value, along with the height pressure value, offers a more accurate fall detection process.

Also, if the wearer moves abruptly, this motion is detected by the accelerometer and with that reading alone a false fall detection might be indicated. But using the accelerometer value along with the gyroscope and pressure sensor values reduces the likelihood of a false positive.

Additional Sensors to Increase Fall Detection Accuracy

The three principal sensors described herein include a tilt sensor, an accelerometer, and a gyroscope. Values measured by additional sensors can increase the fall detection accuracy and reduce false positives. Such additional sensors include: an audio sensor (e.g., a microphone or any sound gathering device, such as augmented home speakers and television speakers), a video sensor (e.g., a camera, including a camera capable of capturing still, moving photos, and videos), a force sensor (a pad for detecting application of a force to the pad).

For example, a microphone may act as a sensor, where the detection of a noise may indicate a fall or the lack if such a noise may indicate that no fall occurred. The microphone may also detect breathing.

A camera may be used to track, for example a particular spot, potentially in low resolution to identify rates of change and the like to provide further data as to the occurrence or not of a fall Sensors can also measure various physiological and biometric parameters (heart rate, respiration rate, muscle tension, blood pressure) and consider these measured values together with the data collected from the various sensors described herein.

The audio sensor can establish an audio link to the monitored person, thereby setting up a voice link. With a family member or first responder on one end of the link, and the monitored person on the other end, the latter can report whether or not she/he has fallen. If the monitored person is unable to vocalize her situation or fails to respond, then the other party can surmise that she needs assistance. This audio link can provide a definitive answer to the question of whether the monitored person has fallen.

Microphones can be easily placed in any wearable device. In another embodiment, microphones can be distributed within the living quarters of the monitored person. These microphones can be always on and listening or voice activated when desired. Having fallen or otherwise unable to access a mobile phone to request help, the monitored person can simply shout to activate the microphone and speak with a party at the other end of the link. The vocal comments can also be gathered as data, along with sensor-measured data (from a wearable device, for example), and sent to a cloud-based (or server-based) fall detection algorithm (in one embodiment an artificial intelligence/machine learning (AI/ML)

In addition to establishing a voice link through the microphone, an activated microphone can detect sounds caused directly by a fall, such as a loud "thump" or "crash." That audio signal is analyzed by the PERS, perhaps by comparison with stored "thump" and "crash" sounds, thereby adding more input data for more accurately determining whether the person has fallen. If no "thump" or "crash" sound is heard through an open microphone, then likely the monitored person has not fallen.

A hearing aid has been identified as a wearable PERS, and that device can be easily modified to also function as a microphone. Headphones that often include both microphone and speakers (both wired and wireless (e.g., based on the Bluetooth standard)) can also serve as wearable PERS and as a microphone.

Similarly, a video link provides video information from which the status of the monitored person can be easily determined. For example, the video can provide data for determining the initial height and distance differential at the time when the monitored person fell. The video can also provide information from which the location of the monitored person can be determined.

Finally, a properly placed force sensor can also supply useful information to detect a fall. For example, if the pad is placed on the person's back and if he fell onto the floor with his back striking the floor, the force sensor produces a signal representative of the force applied to it. Of course, the person can fall and land in many different positions and thus it may be advantageous to use several such force sensors positioned at various locations on the body of the monitored person.

If battery capacity and the availability of power is a concern relative to a PERS, a schedule can be determined for activating and deactivating certain ones of the sensors. The algorithm can be manually created or adjusted, or based on the activity level and location of the monitored person. In an AI/ML implementation, the engine learns to create or adjust the battery life of the PERS unit based on the activity level, location, re-occurrence, time of day, etc. so that the battery usage is lower at times of low activity, but battery capacity is available during high activity periods.

Multiple Sensors for Tentative and Definitive Fall Detection

Each of the sensors in a PERS can operate in conjunction with different thresholds. That is, certain motion detected by the accelerometer may not generate a tentative fall indication, if the accelerometer value does not exceed a first threshold. The threshold values can be established by measuring the sensor values associated with normal wearer motion; slow movement may simply indicate that the wearer is walking, while abrupt acceleration or motion may indicate that the wearer has fallen. The normal or typical (no fall) sensor values can be determined during a test or pre-operational period, during which multiple sensor values are measured during routine wearer activities. The sensor threshold values are then established beyond those values that indicate simple motion by the wearer. Clearly the sensor threshold values must be empirically established and personalized for each wearer.

Sensor values can be measured repeatedly, with the measurement rate determined by the time of day, for example. During the night time hours when the wearer is sleeping, less frequent measurements are needed. But during her active day, all sensors can measure their respective parameter more frequently.

In some embodiments, a fall detector as described herein operates in a computationally intensive environment, requiring more than simple comparators for comparing sensed values against threshold values. The algorithm controlling operation of the fall detector can be written to employ different threshold values for the different sensors at different times of the day and set forth relationships between the threshold values of the sensors. For example, if a first sensor measures a value of X, this activates a second sensor and the threshold value for the second sensor is Y. Thus, if the second sensor measures a value greater than Y, a fall is indicated. However, if the first sensor measures a value A, the threshold for the second sensor is set at D, which is a higher threshold than Y. According to this scenario, to indicate a fall the second sensor must then measure a value greater than D.

The PERS thresholds must also consider the wearers physical condition. For example, is the wearer agile or someone who moves slowly? Is the wearer young and spry or older and slower? Again, the threshold values can only be determined during an empirical pre-operational phase, during which the thresholds are personally established for each individual wearer. Such values of thresholds may be held in profiles and/or patterns for that individual and may, in aggregate, be represented, for example by an average or mean, in at least one template.

Multiple Sensor Inputs

Various embodiments have been described herein in which the measured or sensed values from one or a few sensors are used, either singly or as a group, to determine whether the wearer has fallen. This concept can be extended to n sensors wherein a subset of the n sensors is relied on to determine whether the fall has occurred. For example, if n sensors are monitoring the wearer, and if the measured values from w of the n sensors indicate that a fall has occurred, then the PERS issues the fall alert. In this case, the metric is if a minimum of w sensors from among the n sensors indicate a fall has occurred, an alert is issued.

The numbers n and w are not uniquely determinable and are dependent on several factors, such as the age and activity level of the wearer. The numbers n and w can be fixed within the PERS or determined and reset by the wearer. Obviously, a smaller difference between n and w suggests the likelihood of fewer false alarms (i.e., a fall detected when the wearer did not fall). While a larger gap between n and w likely will generate more false alarms.

Also, with a plurality of sensors in the PERS, selection of the w sensors from among the n sensors can be customized to the wearer and may be manually set by the wearer as desired, in part dependent on the expected activity level of the wearer. The number w and specifically which sensors are included in the group of w sensors can also be configured automatically by an AI/ML algorithm that receives and processes the measured data. Of course, with an AI/ML-based embodiment it is not necessary for the monitored person to consider such issues, as the trained algorithm can automatically select and configure the number and specific sensors.

Certain sensors may be configured, including being deactivated or activated depending on the activity level of the wearer. For example, if the wearer plays tennis every weekday at 3 PM, they can manually disable the tilt sensor before the match begins. Alternatively, an AI/ML algorithm determines (based on a re-occurrence time or other factors) to automatically adjust the fall detector settlings to minimize false positives while the monitored person is engaged in vigorous activities, such as playing tennis. Additionally, the wearer can set the PERS to automatically deactivate the tilt sensor each weekday at 3 PM.

Settings can be configured (manually or according to determinations made by an AI/ML algorithm) for all sensors of the PERS.

All sensors or groups of sensors are not necessarily activated all day, every day. The wearer can customize a time when each sensor is activated or deactivated. A strict pattern of activating and deactivating may not be desirable; customization by the wearer is desired, so long as the efficacy of the PERS is not compromised.

In some embodiments, at least one AI/ML algorithm within and/or accessible to the PERS customizes when each sensor is activated or deactivated, saving the monitored person the burden of manually reconfiguring sensors, whilst managing battery life. The AI/ML, algorithm learns about the repetitive activities or overall activities of the monitored person and makes sensor adjustments as needed.

But there is also a trade-off involved in the selection of n and w. The frequency of false alarms may be reduced if the difference between n and w is small, but the required energy capacity (battery capacity) is greater with more active sensors.

In addition to activating w sensors to acquire measurements, the sequence in which the w sensors are activated is controllable and activation of certain later sensors is conditional upon measured values obtained from previously activated sensors. Again, it is expected that a trained AI/ML algorithm can make these adjustments as needed, and refine the adjustments as it learns more about the activities of the monitored person.

The detection of certain patterns of sensor data, from among a plurality of sensors, may also be used to detect a fall. In particular, when a current data pattern matches a prior data pattern that was followed by a fall, observation of the current pattern is a strong indicator that a fall is eminent. Again, a trained AI/ML algorithm can provide this feature.

The AI/ML component of the PERS (whether cloud-based on otherwise) not only analyzes patterns or indications for a specific individual, but also considers all individuals within a community (or all individuals who have a PERS and send data to the AI/ML algorithm) in search of common precursors for an eminent fall event. For example, such precursors may be represented in the form of templates which can include, in whole or in part, profiles and/or patterns. These may include similar demographics, similar sensor data, and similar data patterns. For example, if a sequence of fall-related activities occurs for the monitored person, that sequence is recorded by the AI/ML algorithm of the NXTD/LogicMark system (assignee of the present application) as representative of a potential fall activity for that individual. However, that sequence could also precede a false positive alert.

But when that data is correlated with data from a larger population (including individuals of similar age, individuals with other similar characteristics, or similar demographics) within the PERS (or even larger aggregate groups whose data is not included in the system) the data may suggest a higher probability that it does in fact represent a fall and not a false alarm (or vice versa). This provides an increase in accuracy of both fall detection and identification of false positives.

For example, if Ms. Simmons' measured data reveals a pattern, but it is uncertain whether the data pattern indicates a potential fall, the data can be correlated with data from an aggregate (or large) community to search for similar prior patterns that have indicated a fall event. In the event of a high correlation, a potential fall is indicated. The wearer is contacted to determine if she fell. She may respond to the question with a "NO." In which case the algorithm is modified to reflect that the data pattern is not necessarily indicative of an expected fall event.

The AL/ML algorithm notes (i.e., learns) that this type of pattern, for Ms. Simmons, at this time of day, in this location, results in a "no fall" determination. The algorithm will also seek to validate this conclusion based on the data pattern to determine whether a repeat of this activity (i.e., similar measured data) results in subsequent situations where Ms. Simmons did not fall. The validation process may include several similar data sets to ensure that the "no fall" determination by the algorithm did in fact correctly determine that Ms. Simmons did not fall.

The AI/ML algorithm can also compare Ms. Simmons data pattern with others in the community to determine the likelihood that a fall occurred or did not occur and then revalidate the algorithm as applied to Ms. Simmons. Thus, the algorithm may determine that similar future data patterns for Ms. Simmons will generate a "no fall" determination.

Additionally, Ms. Simmons data pattern is aggregated and shared across the community, anonymously, so that when a similar data pattern is observed for others of similar age or other similar characteristics to Ms. Simmons (Ms. Smith, for example, a woman of similar age), the system will not indicate this data pattern as preceding a fall event. A validation question is also sent to Ms. Smith to validate that she did not fall and the cycle begins again.

The fall detection system (primarily the at least one AI/ML algorithm) searches for data patterns for an individual to determine that person's unique fall detection patterns. Further, the AI/ML algorithms are executed against other individuals within the community (of similar demographics) to validate whether similar patterns have resulted in falls for others. Therefore, the AI/ML algorithm (embodied as cloud-based software) is constantly learning about what patterns, sensor measurements, sequencing, and the like that indicate a fall is about to occur. This learning process allows the system to note, for example, that when sequence 1, 2, 3 occurs in sensor data, there may be a higher likelihood that blocks 4, 5, and 6 will next trigger in the sensor, which may result in a fall. Or the 1, 2, 3 sequence (or other data) means the fall is likely when considered with similar data of other PERS wearers in the community. Or the sequence 1, 2, 3, is considered with the wearer's past historical data to determine whether that data preceded a fall event. Such analytics can also be applied to determination of when a fall is indicted initially, but does not occur. For example, id sequence 1,2 and 3 occurs the likelihood of a fall may be expected to be N %, however id the time between events 1,2 and 3 differs sufficiently from that sequence when a fall occurs, this can indicate that the fall is less likely, avoiding a fall positive detection.

While sensors typically output a specific measured value, the use of data ranges is also beneficial. Data values within or outside a range represent conditions for activating (or not activating) other sensors. For example, if the measured data from sensor 1 is within a range between X and Y, then sensor 2 is activated. If the measured data is less than X no further measurements are conducted. And if the measured data is greater than Y, sensor 3 is activated. Use of such conditional activation of other (e.g., more sensitive sensors or sensors that are better "fall" predictors) measurably improves the accuracy of fall detection and reduces false positives.

Sensor Directionality

Many sensor types are described herein and commonly used in PERS devices, e.g., gyroscopes for detecting tilt or orientation relative to a reference, accelerometers for detecting speed and acceleration, and pressure measurements for detecting height or a height differential relative to a reference.

Adding a three-dimensional reference space (X, Y, and Z axes) can further increase the accuracy of fall detection. For example, acceleration in primarily the X or Y direction (with minimal movement detected in the Z direction) may indicate that the wearer is walking or jogging. However, a significant change along the Z axis suggests the wearer has fallen. During such a fall slight changes along the X and Y axes would also be expected and further suggest a fall.

Machine Learning and Artificial Intelligence Embodiments

The present invention, in one embodiment, is implemented in at least one machine learning algorithm (i.e., an example of artificial intelligence analysis). These algorithms are dynamic models, implemented in software, that assimilate vast amounts of input data to generate outputs that are typically either binary decisions (e.g., yes/no, accept/reject, etc.) or numeric predictions (e.g., 97%). Machine learning algorithms are differentiated from static computational algorithms by their ability to independently change (i.e., learn) algorithmic details that affect the outcome, with minimal human intervention.

Machine learning algorithms are programmed to self-adjust to reduce errors in its subsequent predictions to better predict the actual outcome. Over time, and many iterations, these algorithms learn to increase the accuracy of their predictions.

Machine learning is a broad umbrella term that covers many different algorithms that each utilize different design strategies. Sub-categories of machine learning algorithms include artificial neural networks, decision trees, random forests, support vector regression and many more, including supervised and unsupervised learning. Many of these algorithms are best suited for specific classes of problems.

Commercially available machine learning algorithms include: TensorFlow (available from Google, Inc. of Mountain View, California), Theano (developed by the Universite de Montreal), Sci-kit learn (Scikit-learn: Machine Learning in Python, Pedregosa et al., JMLR 12, pp. 2825-2830, 2011), or CNTK (available from Microsoft Corporation of Redmond, Washington).

The use of regression techniques may be employed to predict particular values, for example such as those for a set of sensors, where the data provided by the sensor may be evaluated by at least one regression function to create a prediction of the likely data set that sensor will provide at some future time. When a sets of sensors, such as those described herein, each have a predicted data set, these sets may be compared to identify complimentary or conflicting data from the sensors enabling a multi variate approach to determination of the state of, for example, a fall. This enables the detection and remediation of false positives, which may have been indicated by a sensor in isolation, or a set of sensors measuring, for example movement in a X, Y and Z plane.

For example, a decision tree may comprise a decision matrix, which can be represented as a data set for evaluation by other systems and/or may form the basis for activity involving events and/or triggers. One example of such an approach can be a graph-based representation.

In some embodiments, the decision matrix may include thresholds, which can be dynamic, in that the thresholds may change in response to context. For example, the data held in profiles, described herein, may be used to vary the thresholds which are incorporated into the decision matrix.

In some embodiment, support vector machines (SVM) may be used for templet matching, where for example the profile and/or pattern are represented by a template, which can then be used to establish relative similarity between such profiles and/or patterns. For example, if the SVM includes a gaussian kernel, the similarity of X in pattern A may be determined to the X1 in pattern B, where for example, both patterns have a, in whole or in part common template. The SVM may also be used to predict whether a class is either positive or negative, which can represent, for example the state of a set of sensor data.

One implementation of the present invention involves the use of an artificial neural network, which for example, may comprise a number of neural sub networks in any arrangement. In some embodiment, artificial neural networks are collections of "neurons" that are configured in one or more "layers".

Figure 2:
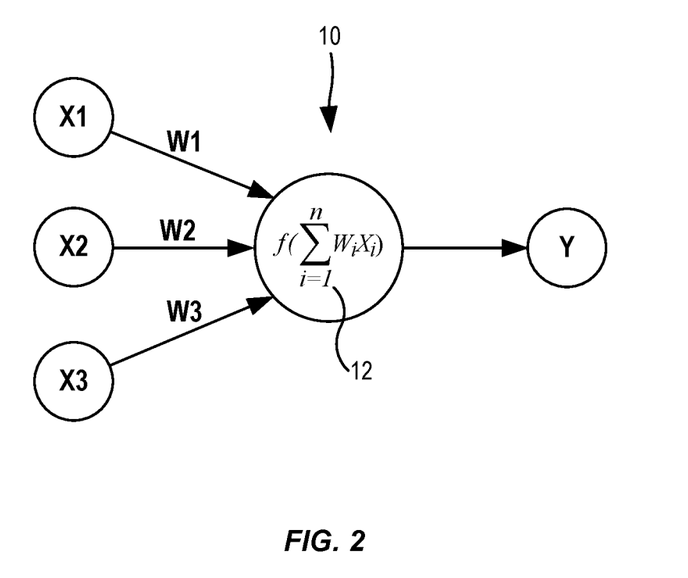
FIG. 2 is a schematic diagram of a simple artificial neural network for determining whether a fall has occurred.

FIG. 2 depicts a single neuron in an artificial neural network. A single neuron 10 embodies a mathematical activation function 12, i.e., a simple static function that converts multiple weighted inputs from sensors to a single output value. The neuron 10 receives input data from sensors X1, X2, X3 to which a weight value weights W1, W2, W3 has been applied. The activation function 12 is applied to the sum of the weighted values, as illustrated. An output Y is the result.

Figure 3:
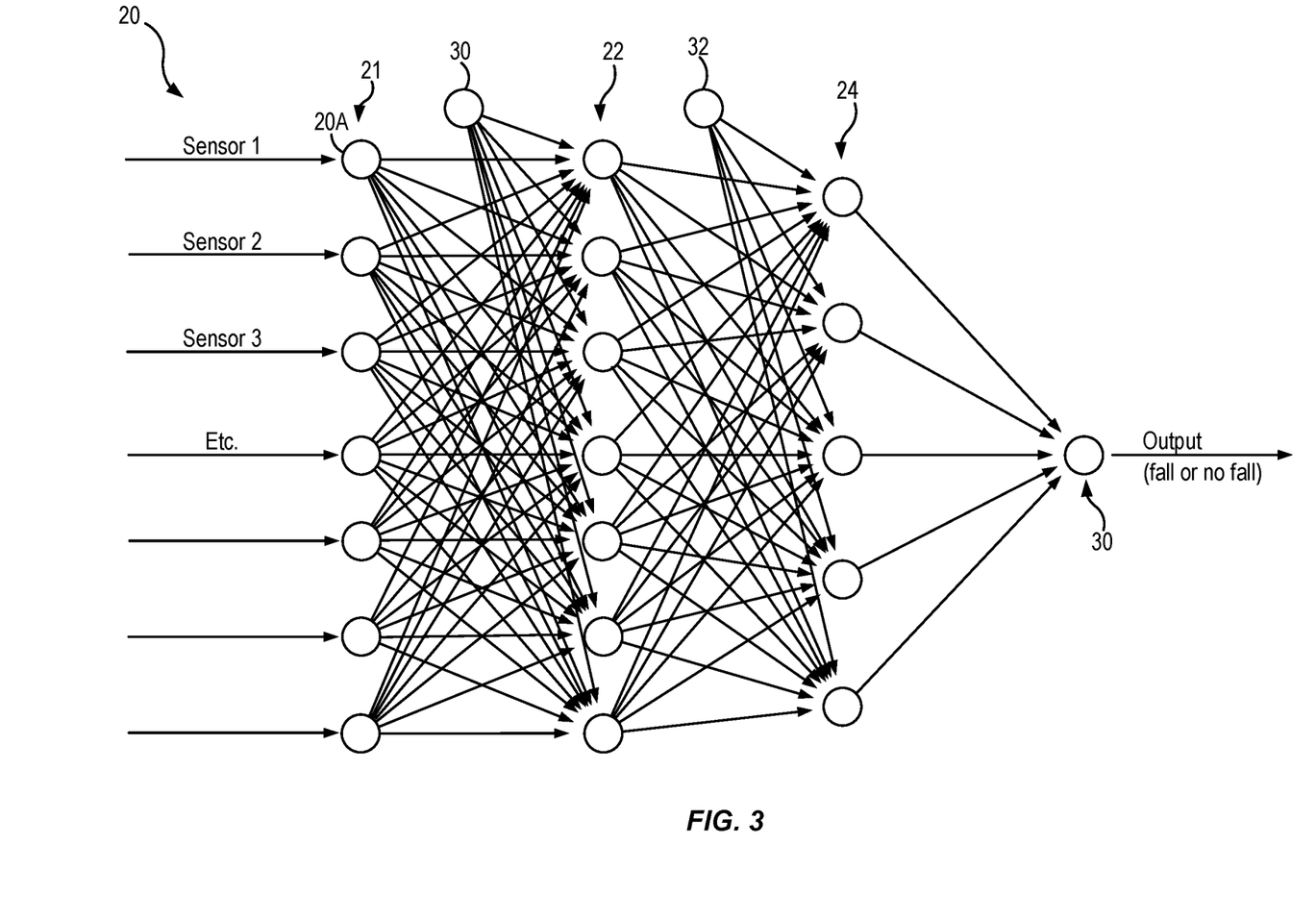
FIG. 3 is a more accurate neural network embodiment for fall detection.

As applied to the present invention, the input data comprises measured values from the fall detector sensors, including, for example, an accelerometer, a gyroscope, and a pressure sensor. And the output Y indicates that a fall occurred or did not occur, which can include a probability weighting factor, such as for example a confidence metric, e.g., 93%. However, this is an oversimplified description of a neural network applied to the present fall detection problem. FIG. 3, described below, is a more accurate neural network embodiment for fall detection.

The specific activation function used in a neural network depends on the type of output desired. Activation functions can be as simple or complex as necessary to adequately represent the combined effect of lower layers of the neural network or the combination of the input data. For instance, predicting a binary classification, such as a fall has or has not occurred, suggests use of a sigmoidal activation function that outputs a 0 or 1. Outputs greater than a threshold (usually 0.5) are predicted to be one category (e.g., a fall has occurred) while outputs below a threshold fall into the other category (e.g., a fall has not occurred). Such categories may be formed from the data held in the profiles described herein.

Regardless of the activation function, the calculated output (Y) can then be passed to another neuron as an input, or it can represent the final output of the complete neural network. One skilled at implementing artificial neural networks can apply the appropriate activation function as determined by the types of inputs and the desired output.

FIG. 2 is a schematic diagram of a simple artificial neural network for determining whether a fall has occurred. A plurality of sensor inputs is shown on the left side of FIG. 2, each input representing a value that is input to each node in a column 21. The plurality of inputs is represented by the sensors described herein and other sensors that can supply information useful in determining whether a fall has occurred.

Each input to the neurons in column 21 is a numerical output (a sensed or measured value) of a specific sensor. The sensor values can be measured continuously or periodically, at a fixed period, at a fixed time each day, a period that varies throughout the day, or a period that is variable as determined by values measured by one or more of the other sensors. Thus, the granularity of the sensor measurements can be determined by the wearer and/or the PERS designer.

As the output values from each node in column 21 (the sensor measurements) are passed to one or more nodes in column 22, they are modified (for example multiplied) by weights assigned from bubble 30. For example, the several lines extending from node 21A represent a value measured by sensor 1. Each is multiplied by a weight (same or different weights applied to each sensor value) from bubble 30 and each terminates on a node in column 22. Thus, a weight value modifies the output value from the node 21A and the weighted value is input to the corresponding node in the column 22.

The process is repeated with various weights multiplied by the sensor output values from column 21; the product of the sensed value and the weight input to each node in column 22. The process is repeated with the outputs from column 22 multiplied by weights supplied from bubble 32; with the resultant products input to each one of the nodes in a column 24. Finally, the output values from the column 24 are combined at a node 30 and the output value from the node 30 indicates that a fall did or did not occur.

Generally, the weight values in FIG. 3 indicate the effect that a sensor reading has on each node in the next column, and ultimately on the final decision that a fall has occurred or has not occurred. Note that the effect of each value from column 21 is likely different for each node in the subsequent column as reflected by different weight values. Further, note that the weight could be zero if an input feature has no effect on the next node.

Bubbles 30 and 32 provide weights for each node in columns 21 and 22. These weights may be based on results from prior iterations through the neural network 20 and thus establish a starting point (or constant adjustment) for the input value in each node. As the algorithm is trained (or later updated) the weight values are changed to optimize the outcome from the neural network so that the accuracy of a fall detection is improved and consequently the identification of false positives is also improved.

As shown in FIG. 3, an artificial neural network typically entails a complex amalgamation of individual neurons with different weights applied to the output of each neuron, diverse input data, and a plurality of activation functions (as represented by the nodes) to accurately predict an outcome.

A prediction error is defined as the difference between the network output (e.g., the fall occurred) and the actual output (e.g., the fall did not occur). This approach significantly improves the detection of false positives. For example, a loss function computes the magnitude and direction of the prediction error. The prediction error is then back-propagated through the network, updating the weights applied to the output from each neuron to reduce prediction errors during subsequent iterations of the neural network. Thus, the neural network is not a static function, but one that changes with each training episode.

In one scenario, the initial weights may be randomly selected for each neuron. Training is then conducted using historical data until the weights converge to values that work sufficiently well for matching input data (the sensor values) with the correct output data (the fall did or did not occur). Once the machine learning algorithm has been "taught" by selecting appropriate weights to reduce errors in the predicted fall or no-fall determination, the processor executes the algorithm based on real-time sensor inputs. Training the algorithm can continue even after it has been put to use by the optimization and back-propagation techniques described herein (which is generally referred to as updating the algorithm).

A neural network trained with many observations of historical data can achieve robust and accurate predictive capabilities relative to a fall or no-fall determination increasing the accuracy of fall detection and consequently a reduction in false positives which could trigger events. Once a network has learned a stable pattern of prediction, it can be deployed to make real time predictions. Unlike the algorithm training process, employing the algorithm for fall prediction is very quick and allows the algorithm to administer decisions in near real time. Furthermore, training (generally referred to as updating the algorithm once the algorithm has been deployed in operation) can be continued given new data even after the algorithm is operational and can be further enhanced when used in conjunction with reinforcement learning techniques to optimize learning to increase the accuracy of the fall or no-fall determination.

Many different sensor types and analyses processes have been described herein for collecting and analyzing data possibly indicative of an anticipated fall. Generally, such sensors comprise physical sensors outputting a signal using hardware and software elements. In one embodiment such sensors are affixed to or integrated in a wearable device. In one embodiment the measured data is sent to a cloud-based AI/ML algorithm for processing and fall detection. A service provider (business entity) can provide the algorithm, receiving measured data from the monitored person and processing the data through its algorithm. If the algorithm determines that a fall occurred the service provider issues notifications to parties identified by the monitored person.

The previous description of the embodiments is provided to enable any person skilled in the art to practice the disclosure. Thus, the present disclosure is not intended to be limited to the embodiments shown herein, but is to be accorded the widest scope consistent with the principles and features disclosed herein.

What is claimed is:

1. A wearable device comprising:
   a machine-learning fall detection processor;
   a non-transitory computer-readable medium with a database configured to store an expected activity level of the wearer;
   a plurality of motion sensors, each motion sensor having an individual fall motion threshold, the motion sensors configured to send a fall motion signal to the fall detection processor when the individual fall motion threshold is exceeded;
   at least one height sensor having a fall height threshold, the at least one height sensor configured to send a fall height signal to the fall detection processor when the fall height threshold is exceeded;
   a force sensor having a force threshold, the force sensor configured to send a force signal to the fall detection processor when the force threshold is exceeded;
   the fall detection processor is configured to issue an alert when a minimum number of sensors from among a total number of sensors of the plurality of motion sensors, the at least one height sensor, and the force sensor indicate a fall has taken place;
   wherein the minimum number of sensors is set automatically by fall detection processor based in part on the expected activity level of the wearer; and
   the fall detection processor updates the expected activity level of the wearer stored in the database with an actual activity level of the wearer.

2. The wearable device of claim 1,
   wherein the fall detection processor is further configured to alter the minimum number of sensors based in part on the expected activity level of the wearer.

3. The wearable device of claim 2,
   wherein the fall detection processor is further configured to adjust the individual fall motion threshold, the fall height threshold, or the force threshold based in part on the expected activity level of the wearer.

4. The wearable device of claim 3,
   wherein fall detection processor is further configured to turn on or off a sensor based in part on the expected activity level of the wearer.

5. The wearable device of claim 4 further comprising:
   a user interface to allow the wearer to adjust the expected activity level of the wearer.

6. The wearable device of claim 5 further comprising:
   wherein the user interface includes a microphone with an audio processor that has an impact detection threshold, the audio processor is further configured to send an impact signal to the fall detection processor when the crash detection threshold is exceeded;
   wherein the total number of sensors further includes the microphone.

7. The wearable device of claim 5 further comprising:
   wherein the motion sensor is a gyroscope sensor that has a tilt detection threshold, the gyroscope sensor is further configured to send a tilt signal to the fall detection processor when the tilt detection threshold is exceeded;
   wherein the total number of sensors further includes the gyroscope sensor.

8. The wearable device of claim 5, wherein the fall detection processor adjusts the expected activity level of the wearer based on the time of day.

9. The wearable device of claim 5, wherein the fall detection processor uses a regression technique, a decision tree or a decision matrix to help determine the expected activity level of the wearer.

10. The wearable device of claim 5, wherein the fall detection processor remediates false positive fall signals by isolating a sensor.

11. The wearable device of claim 5, wherein the fall detection processor uses support vector machines (SVM) for template matching to help determine the expected activity level of the wearer.

12. The wearable device of claim 5, wherein the fall detection processor is a neural network.

13. A fall detection method of a wearable device comprising:
    store an expected activity level of a wearer in a database on a non-transitory computer-readable medium;

receiving a fall motion signal from a plurality of motion sensors, each with a fall motion threshold, by a fall detection processor when the individual fall motion threshold is exceeded;

receiving a fall height signal from at least one height sensor having a fall height threshold by the fall detection processor when the fall height threshold is exceeded receiving a force signal from a force sensor having a force threshold, by the fall detection processor when the force threshold is exceeded;

issuing an alert with the fall detection processor when a minimum number of sensors from among a total number of sensors of the plurality of motion sensors, the at least one height sensor, and the force sensor indicate a fall has taken place;

wherein the minimum number of sensors is set automatically by fall detection processor based in part on the expected activity level of the wearer; and updating, with the fall detection processor, the expected activity level of the wearer stored in the database with an actual activity level of the wearer.

14. The fall detection method of claim 13,
wherein the fall detection processor is further configured to alter the minimum number of sensors based in part on the expected activity level of the wearer.

15. The fall detection method of claim 14,
wherein the fall detection processor is further configured to adjust the individual fall motion threshold, the fall height threshold, or the force threshold based in part on the expected activity level of the wearer.

16. The fall detection method of claim 15,
wherein fall detection processor is further configured to turn on or off a sensor based in part on the expected activity level of the wearer.

17. The fall detection method of claim 16 further comprising:
adjusting the expected activity level of the wearer with input from a user interface.

18. The fall detection method of claim 17 further comprising:
wherein the user interface includes a microphone with an audio processor that has an impact detection threshold, the audio processor is further configured to send an impact signal to the fall detection processor when the crash detection threshold is exceeded;

wherein the total number of sensors further includes the microphone.

19. The fall detection method of claim 17 further comprising:
wherein the motion sensor is a gyroscope sensor that has a tilt detection threshold, the gyroscope sensor is further configured to send a tilt signal to the fall detection processor when the tilt detection threshold is exceeded;

wherein the total number of sensors further includes the gyroscope sensor.

20. A non-transitory computer readable storage medium encoded with data and instructions, when executed by a fall detection processor causes a wearable device to:

store an expected activity level of a wearer in a database on the non-transitory computer-readable medium;

receive a fall motion signal from a plurality of motion sensors, each with a fall motion threshold, by a fall detection processor when the individual fall motion threshold is exceeded;

receive a fall height signal from at least one height sensor having a fall height threshold by the fall detection processor when the fall height threshold is exceeded receive a force signal from a force sensor having a force threshold, by the fall detection processor when the force threshold is exceeded;

issue an alert with the fall detection processor when a minimum number of sensors from among a total number of sensors of the plurality of motion sensors, the at least one height sensor, and the force sensor indicate a fall has taken place;

wherein the minimum number of sensors is set automatically by fall detection processor based in part on the expected activity level of the wearer; and the fall detection processor updates the expected activity level of the wearer stored in the database with an actual activity level of the wearer.

* * * * *